(12) United States Patent
Sanderson et al.

(10) Patent No.: US 7,070,570 B2
(45) Date of Patent: Jul. 4, 2006

(54) METHOD AND MEANS OF PHYSIOLOGICAL MONITORING USING SONIFICATION

(76) Inventors: Penelope Margaret Sanderson, St. Lucia (AU); Marcus Watson, Sherwood (AU)

(*) Notice: Subject to any disclaimer, the term of this patent is extended or adjusted under 35 U.S.C. 154(b) by 0 days.

(21) Appl. No.: 10/488,150

(22) PCT Filed: Aug. 26, 2002

(86) PCT No.: PCT/AU02/01149

§ 371 (c)(1),
(2), (4) Date: Feb. 27, 2004

(87) PCT Pub. No.: WO03/017838

PCT Pub. Date: Mar. 6, 2003

(65) Prior Publication Data

US 2004/0243016 A1    Dec. 2, 2004

(30) Foreign Application Priority Data

Aug. 29, 2001 (AU) .................... PR 7339

(51) Int. Cl.
*A61B 5/00* (2006.01)
(52) U.S. Cl. .................... 600/532; 73/23.3; 422/84
(58) Field of Classification Search ........ 600/529–538; 73/23.3; 422/84
See application file for complete search history.

(56) References Cited

U.S. PATENT DOCUMENTS

| | | | | |
|---|---|---|---|---|
| 4,063,550 A | * | 12/1977 | Tiep | 600/529 |
| 4,413,632 A | * | 11/1983 | Schlessinger et al. | 600/529 |
| 5,069,220 A | * | 12/1991 | Casparie et al. | 600/532 |
| 5,355,893 A | * | 10/1994 | Mick et al. | 600/532 |
| 5,730,140 A | * | 3/1998 | Fitch | 600/514 |
| 5,738,106 A | * | 4/1998 | Yamamori et al. | 600/532 |
| 6,076,005 A | * | 6/2000 | Sontag et al. | 600/413 |

* cited by examiner

*Primary Examiner*—Robert L. Nasser
(74) *Attorney, Agent, or Firm*—Brooks Kushman, P.C.

(57) ABSTRACT

The invention resides in a respiratory sonification monitoring method and system for monitoring respiration in a subject including the use of capnometric means for measuring carbon dioxide concentrations, flowmeter means for measuring gas flow and volume of gas; means adapted to process into digital information, signal output from the capnometric means and the flowmeter means, sound synthesizer means adapted to convert the digital information into synthesised audio output, wherein, changes in respiratory flow during inhalation and exhalation, and changes in end tidal carbon dioxide concentrations (ETC02) and cumulative tidal volume (cumVt) of the subject can be represented as changes in synthesised sound heard through a loudspeaker, headphone or ear piece.

14 Claims, 8 Drawing Sheets

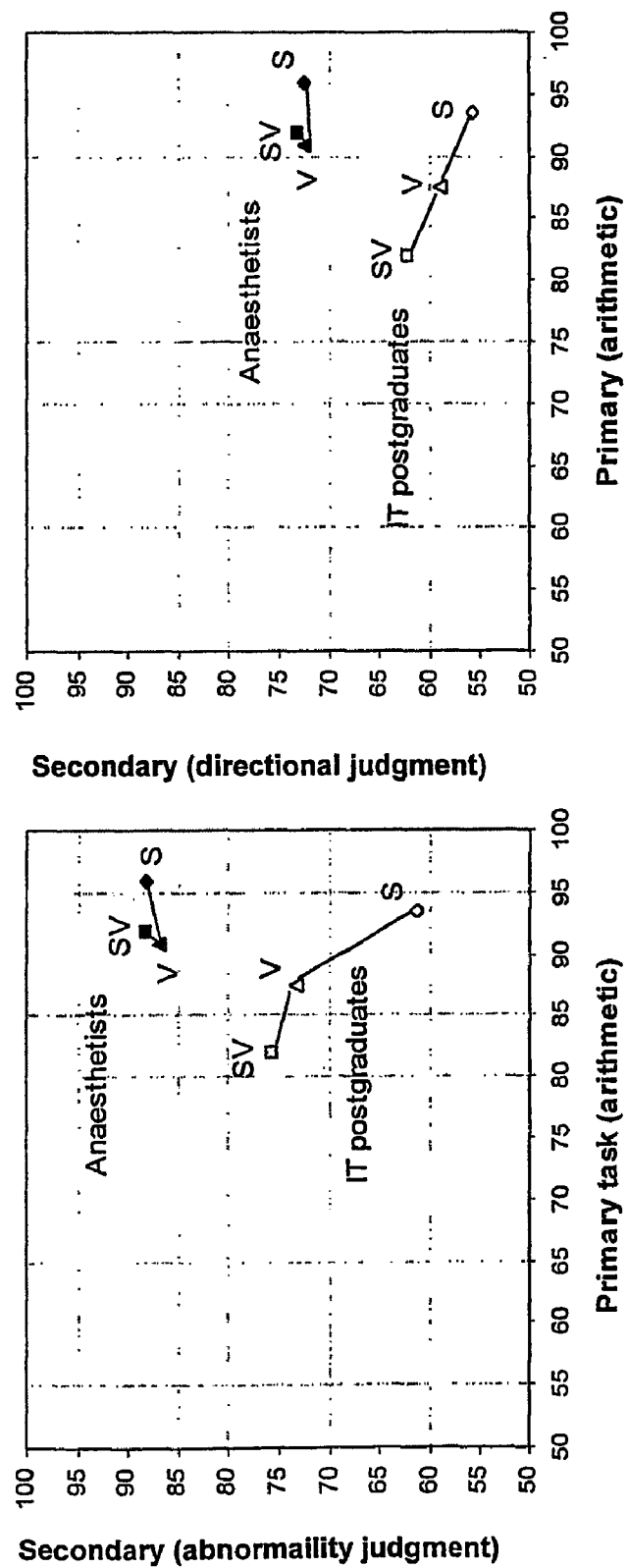

METHOD AND MEANS OF PHYSIOLOGICAL MONITORING USING SONIFICATION

FIELD OF THE INVENTION

The present invention relates to a means and a method of monitoring human respiration and gas exchange. In particular but not exclusively, it relates to the sonification of respiratory parameters to monitor human respiration and gas exchange during anaesthesia and intensive care.

BACKGROUND OF THE INVENTION

Various respiration detection and/or monitoring devices have been suggested and/or utilised in a variety of settings previously, and have included devices utilising impedance plethysmography, inductance plethysmography, aural monitoring, EMG or EKG monitoring, strain gauges or the like. These devices all have different limitations, including undue complexity for some uses, inability to monitor, or distinguish between, different types of respiratory and/or unrelated events such as upper airway obstructions, breath holding, sighing, yawning and artefact both of a mechanical and electromagnetic nature. Despite these limitations these devices are still used today as previous studies have established the crucial importance of respiratory monitoring for patient safety.

In recent years, pulse oximetry and capnography have been used to monitor heart rate and oxygen saturation. Pulse oximetry is described in U.S. Pat. No. 4,653,498 and utilises sonification. Although there have been experimental versions of sonifications designed to convey information about respiratory functioning (Fitch & Kramer, 1994; Loeb & Fitch, 2000) all have been in the context of a reworking of cardiovascular sonification and all have been experimental in nature. There has been no comparative study of the effectiveness of different respiratory sonifications under controlled conditions and no study of the effectiveness of respiratory sonification when other tasks must be performed, as is often the case in the operating theatre. Accordingly, there is no respiratory sonification in regular clinical use in health care or other physiological monitoring contexts.

The only devices used in the clinical context that provide auditory information about respiration are the ventilator and the precordial stethoscope. Ventilators are used in anaesthesia and intensive care contexts to support a patient's respiration, and usually deliver a base mixture of air and oxygen. In the anaesthesia context, a variety of anaesthetic gas can be added such as nitrous oxide, isoflurane, sevoflurane, halothane, and the like. Ventilators work in several modes, which can be roughly distinguished as follows:

1). spontaneous patient respiration;
2). manually assisted patient respiration; and
3). Machine-supported patient respiration.

Spontaneous patient respiration involves unassisted patient respiration, where respiration rate, airway pressure, tidal volume, volume flow, and end tidal carbon dioxide ($ETCO_2$) can be measured. Manually assisted patient respiration involves patient respiration that is assisted by the anaesthetist who manually forces gas into the patient's lungs at regular intervals by squeezing a gas-filled bag attached to the ventilator.

Machine-supported patient respiration has a variety of modes relating to such things as aspects of the lung pressure that is maintained, the volume of gas that is delivered, the respiration rate maintained, the proportion of machine breaths that are given per patient breath if there is any patient respiration, and the ratio of the duration of inhalations to the duration of exhalations. Under machine ventilation, gas is automatically delivered to the patient through a mechanically-driven bellows.

In older anaesthesia machines and ventilators, the bellows was in plain view, and its operation could be reasonably clearly heard alongside other ambient noise. However, in newer anaesthesia machines and ventilators, there has been a trend to make the bellows, operation quieter and to place the bellows out of sight. Therefore the informal information provided about machine-supported patient respiration that an older generation of ventilators provided is starting to disappear, with possible adverse consequences.

The precordial stethoscope incorporates a sensor affixed to the patient's chest, connecting tubing as seen in a normal stethoscope, and typically a single ear piece worn by the anaesthetist or critical care provider. The precordial stethoscope amplifies and, delivers to the ear high-fidelity, naturally generated sound generated by the heart and the lungs. Not only can respiration rate and the ratio of inhalation to exhalation be heard and depth of respiration inferred, but also a wide variety of lung sounds and qualities that suggest inappropriate intubation (positioning of a breathing tube), blockages and occlusions, respiratory abnormalities and lung diseases. However there are disadvantages to the precordial stethoscope as a means of continuously monitoring patient respiratory functioning. For example, the precordial stethoscope provides no information about $ETCO_2$, which relies upon the presence of capnometry; the sensor and ear piece need to be continuously in place for monitoring to take place, which may not always be convenient.

Accordingly, neither the ventilator nor the precordial stethoscope provides a satisfactory means of monitoring respiration in a subject. Therefore, there is a real need for a means of monitor human respiration, especially during anaesthesia and intensive care.

The applicant has now developed a respiratory sonification means and method that overcomes or at least alleviates some of the problems highlighted above.

OBJECT OF THE INVENTION

It is therefore the object of the present invention to overcome or alleviate some of the limitations and disadvantages of prior art respiratory monitoring system during anaesthesia and intensive care or to at least provide the public with a useful choice.

STATEMENT OF THE INVENTION

In one aspect, the invention resides in a respiratory sonification monitoring system for monitoring respiration and/or gas exchange in a subject including in combination capnometric means for measuring respiratory carbon dioxide concentrations, flowmeter means for measuring gas flow and volume of said gas flow by the integration of the gas flow with respect to time, signal processing means adapted to process into digital information, signal output from the capnometric means and the flowmeter means, sound synthesizer means adapted to convert said digital information into synthesised audio output, wherein in use, changes in respiratory flow during inhalation and exhalation, and changes in end tidal carbon dioxide concentrations ($ETCO_2$) and cumulative tidal volume (cumVt) of the subject can be represented and monitored as changes in synthesised sound heard through a loudspeaker, headphone or ear piece.

Preferably, the capnometric means is an electronic carbon dioxide monitor with signal output means whereby end tidal carbon dioxide concentrations ($ETCO_2$) can be measured and recorded.

Preferably, the flow meter means is an electronic respiratory flow meter wherein cumulative volume measurements can be calculated by the electronic integration of the gas flow signal over a given time interval.

Preferably, the signal processing means is an analogue to digital signal converter wherein analogue signals from the capnometric means and the flow meter means are converted into digital information.

Preferably, the sound synthesizer means has audio pre-amplifier means which conditions the digital information and converts it to a synthesised audible tone which can be heard through a loudspeaker, headphone or ear piece.

Preferably, inhalation is represented as an upper note of a musical third interval and exhalation is represented as the lower note that comprise a pair of tones.

Preferably, end tidal carbon dioxide concentration ($ETCO_2$) is represented by a change in relative pitch across respiratory cycles wherein the pitch of the exhalation tone is set at a minor third interval below that of the inhalation tone, and wherein a high $ETCO_2$ would be represented by a pair of tones at a high pitch and low $ETCO_2$ would be represented by the pair of tones in at a low pitch.

Preferably, there are five regions of pitch changes wherein the lowest pitch level reflects end tidal carbon dioxide concentrations below an arbitrarily low $ETCO_2$ concentration value and the highest pitch reflects end tidal carbon dioxide concentrations values above an arbitrarily high $ETCO_2$ concentration value.

Preferably, the measured end tidal carbon dioxide levels can be graphically represented as a frequency modulation of the minor third interval note pairs of inhalation and exhalation tones.

Preferably, cumulative tidal volume (cumVt) is calculated by integrating volume flow (Vf) over time and is represented by sound intensity (loudness) and/or sound quality (timbre or brightness) and wherein the cumulative tidal volume (cumVt) can be represented by the amplitude of more than one spectral component of the sound, resulting in perceptible differences in timbre or harmonic brightness of the audible tones.

Preferably, there is user interface means typically a volume control to control and adjust the overall volume of the sonification.

Preferably, the user interface means is an electronic or electromechanical volume control means.

Preferably, the respiratory monitoring apparatus is not necessarily used in isolation but alongside prior art pulse oximetry systems.

In another aspect, the invention resides in a method of monitoring human respiration and gas exchange during anaesthesia or intensive care including the steps of connecting a flow meter to an anaesthesia circuit to measure the rate at which gas is flowing into (inhalation) and out of (exhalation) a patient's lungs, connecting a capnometer to the anaesthesia circuit to measure carbon dioxide concentrations, inclusive of end tidal carbon dioxide concentrations ($ETCO_2$) at the end of each exhalation, processing signals from the flow meter and the capnometer by signal processing means into digital information, converting the digital information by sound synthesizer means into audio output, wherein, the onset and offset of inhalation and exhalation are represented as changes in tone of a synthesised musical note, the value of cumulative tidal volume (cumVt) is represented as sound intensity (loudness) and/or sound quality (timbre or brightness) of the tone, and end tidal carbon dioxide levels ($ETCO_2$) are represented by relative changes in pitch across respiratory cycles, wherein the pitch of the exhalation tone is set at a minor third interval below that of the inhalation tone.

BRIEF DESCRIPTION OF THE FIGURES

FIGS. 7a and 7b show the primary task (arithmetic) performance and secondary task (patient monitoring) judgements of physiological abnormality (FIG. 7a) or direction of physiological change (FIG. 7b).

FIG. 8a shows abnormality judgements and FIG. 8b shows directional judgements.

DETAILED DESCRIPTION OF THE INVENTION

Our respiratory sonification collects digital information about each of several respiratory parameters from a patient monitoring system or ventilator. It then maps the information about each respiratory parameter into a specific value of a specific auditory dimension that has been designated for that respiratory parameter.

The onset of inhalation, and therefore of a new breath, and the duration of inhalation and the duration of exhalation are all determined from ventilator sensors such as the volume flowmeter. The onset of inhalation and the onset of exhalation define the periods over which component parts of the respiratory sonification should be played (see arrows 1 and 2 on FIG. 1).

Any movement of air in or out of the lungs is represented as a base sound stream. In our initial investigations we have used a pure tone as the base sound stream. However other waveforms or combinations of waveforms could be used as long as they do not sound so similar to natural respiration that they might be confused for it (see points below).

The difference between movement into the lungs (inhalation) and out of the lungs (exhalation) is represented as a consistent difference in sound quality. In our initial investigations we have distinguished inhalation and exhalation as follows. Inhalation is represented as the upper note of a musical third interval and exhalation is represented as the lower note (see point 3 on FIG. 1). However other ways of acoustically separating inhalation and exhalation could be used, such as other musical intervals.

$ETCO_2$ is always measured at the end of a breath. Therefore it is not possible to provide information (auditory or visual) about CO2 concentration related to the exact breath on which it was measured. $ETCO_2$ is only available after the breath on which it was measured. Therefore the $ETCO_2$ of a breath at time t-1 is mapped to the sonification of the breath at time t. The relation between $ETCO_2$, other variables, and the sonification produced is shown in FIG. 1.

Figure 1:
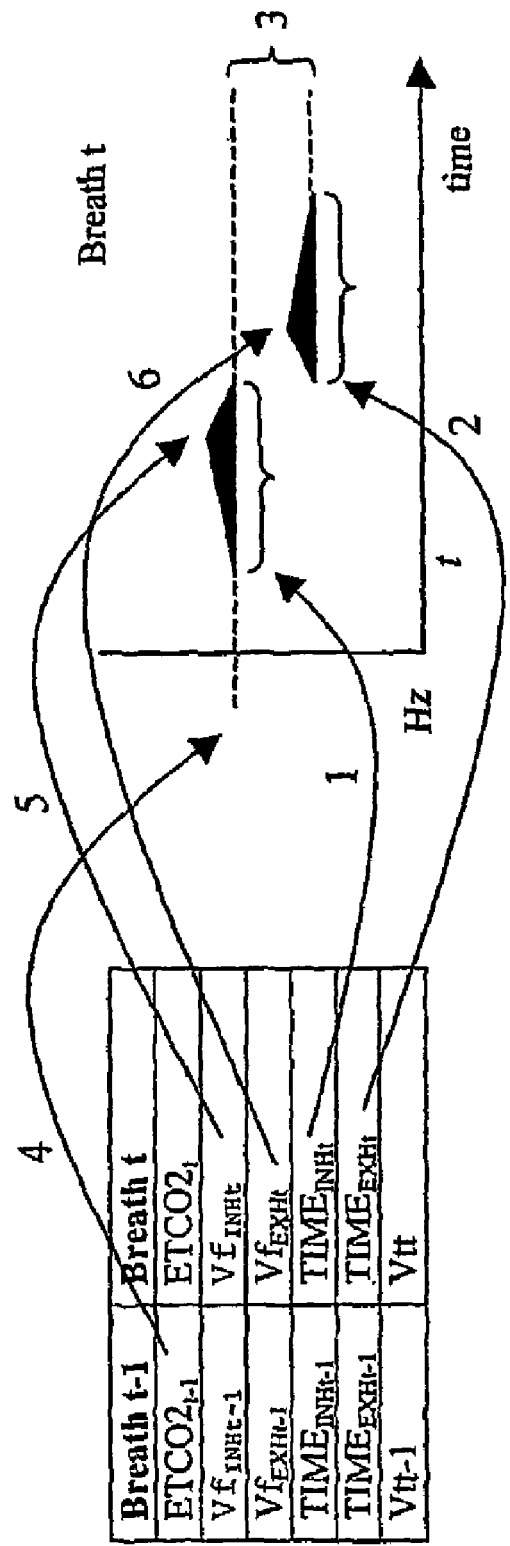
FIG. 1 shows the mapping of respiratory parameters into dimensions of the respiratory sonification. The height of the inhalation and exhalation lines (black areas) symbolically represent increase in sound brightness and intensity rather than changing spectral band in the vicinity of the fundamental frequency of the base sound.

Our respiratory sonification maps $ETCO_2$ into the relative pitch of the inhalation and exhalation sound (see point 4 on FIG. 1). In the example we have tested, $ETCO_2$ is represented as a frequency modulation of the minor third interval produced by the inhalation and exhalation. In other words, inhalation and exhalation are always in the same musical relationship or the same distance apart in pitch, but the relative pitch of the inhalation exhalation pair varies with $ETCO_2$.

Finally, the respiration sonification needs to indicate tidal volume. Tidal volume (Vt) is a similar parameter to $ETCO_2$—it is only known at the end of the breath. Therefore, if Vt is to be mapped to the sonification, like $ETCO_2$ it will be giving information about the breath immediately prior. We propose using instead volume flow (Vf) or the reading of the flowmeter which can be fitted to the Y-piece of the anaesthesia circuit (see points 5 and 6 on FIG. 1). Vf gives immediate information about the rate at which gas is flowing to the patient's lungs during the current breath, and so is available to be mapped to the current breath sonification in real time. Vf integrated over time gives CumVt. We propose that CumVt be mapped into a mixture of sound intensity and sound quality (timbre or brightness). At present we have evaluated CumVt (against Vt—see Example 1) both mapped only into sound intensity (see Example 1). FIG. 1 shows that the inhalation and exhalation are depicted as being broader near their respective midpoints. This is not to be taken literally as a broadening of the sound spectrum with CumVt, but instead to indicate the presence of greater sound intensity and/or an increase in the harmonic complexity (increased presence of the harmonics of the base frequency of the sound).

The significance of our respiratory sonification compared with prior examples lies in the following factors.

Our respiratory sonification is intended to work alongside existing commercial pulse oximetry systems rather than being part of a system for sonifying a broader range of physiological variables including cardiovascular variables.

In previous art it has not been noted that because capnometry (end tidal carbon dioxide level) and tidal volume (breath volume) are not known until the end of the current breath, then they can only be sonified in the next breath. We therefore present a method for sonifying volume flow of the current breath, rather than sonifying tidal volume of the previous breath. This provides immediate acoustic information to the listeners about respiratory functioning on the current breath. Within each inhalation and exhalation, volume flow is sonified so that it ranges from zero to the maximum seen for inhalation and exhalation rather than playing at a constant sound intensity and brightness. The distance the sound travels from its baseline therefore provides useful relative information rather than requiring the listener to judge overall tidal volume on the basis of an absolute and constant presentation of a specific sound intensity and brightness.

Because a sonification can never capture full array of clinical signs associated with respiration, we propose that using complex naturalistic sounds to represent respiration, such as a breathing or white noise sound, may be actively misleading. We therefore present as the base sound for respiratory sonificationan artificial sound that will not run the danger of being mistaken for the patient's actual breathing.

The distinction between inhalation and exhalation is presented as two pure notes played in sequence, with constant acoustic differentiation between them. Our respiratory sonification operationalises this with the first note (inhalation) as the upper note of a musical third and the second note (exhalation) as the lower note of a musical third. Variants are possible.

Therefore our sonification is not a method and interface for allowing the user to select which variables are sonified or how they are sonified, as in U.S. Pat. No. 5,730,140. A major distinction with U.S. Pat. No. 5,730,140 is that the present method, unlike the former, is not based on generating or simulating a realistic bodily sound, but relies on the production of a synthesised audible tone. The use of synthetic tonal sound has two major advantages over the simulation of natural breathing sounds. First, it is much more free from masking by other sounds found in the operating theatre, such as suctioning. Second, the tonal sound avoids the incorrect association caused by operators mistaking the sound as an audification (a natural sound that has simply been amplified and transformed) of the patient's natural chest sounds. Third, specifying the mapping of respiratory parameters to sound dimensions, rather than allowing the anaesthetist to select the mapping of physiological parameters to sound dimensions, supports other operating theatre staff members' awareness of the patient's physiological state because non-anaesthetists will be able to learn to identify abnormal patient states from the combination of the respiratory and pulse oximetry sonifications. Furthermore, U.S. Pat. No. 5,730,140 does not provide information whereby $ETCO_2$ is represented by changes in relative pitch across the respiratory cycle such that the exhalation tone is set at a minor third interval below that of the inhalation tone and wherein high value $ETCO_2$ changes are represented by a change to a high pitch and low value $ETCO_2$ changes by a change to a low pitch. In addition, the calculation of cumVt is also not possible with U.S. Pat. No. 5,730,140.

Engineering Block Diagrams and Sound Mapping

Our respiration sonification uses two sensing systems: capnometry and the volume flowmeter. It takes digital output from these systems, adjusts the output to the ranges needed, maps the result to a dimension of sound accessible through a sound synthesizer, converts the information to sound using a sound synthesizer, and then provides audio output either through loudspeakers, headphones, or through an ear piece worn by the anaesthetist. There are many possible sound synthesis solutions for rendering our respiration sonification. Our claim is for the design of the sonification itself rather than the means of implementing it.

Capnometry exists on most anaesthesia machines and most ventilators. A sensor in the breathing circuit provides a continuous signal for analysis of the concentration of CO2 in expired gases and an end tidal CO2 value is supplied by end expiration. Our respiratory sonification system will use the capnography output from a serial port or through internal software communication, as it is expressed in mmHg (millimeters mercury) (see box A of FIG. 2).

Figure 2:
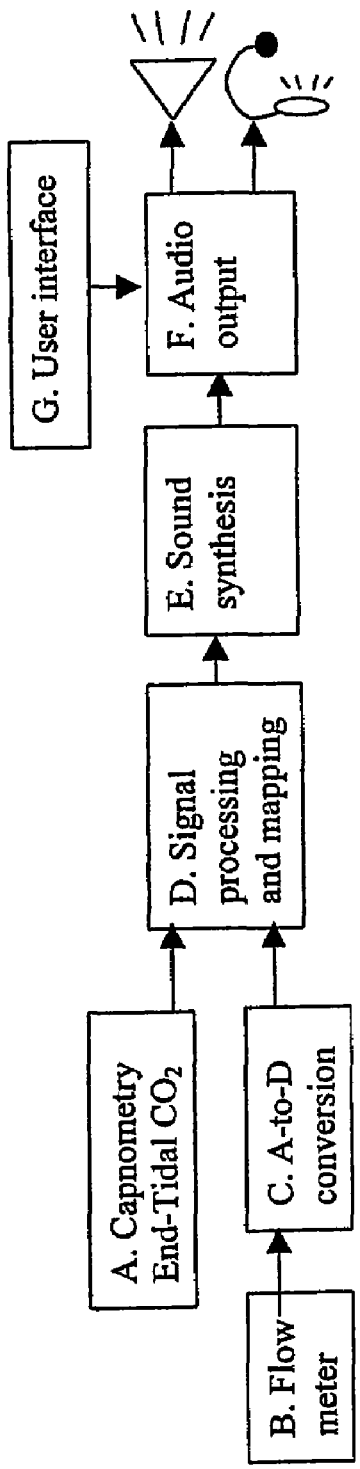
FIG. 2 shows a block diagram of possible implementation of the respiratory sonification.

Volume flow can be measured through a standard flowmeter that can be connected into the Y-piece of the external breathing circuit (see box B of FIG. 2). The analogue signals from the flowmeter are converted into continuous digital outputs for inhaled or inspired volume flow (Vfinh) and for exhaled or expired volume flow (Vfexh) and are expressed as a flowrate of ml/minute (milliliters per minute) (see box C of FIG. 2). Volume flow is integrated over time to yield cumulative Vt, which is the value mapped to the sonification parameter as shall be discussed.

The signal processing and mapping unit (see box D of FIG. 2) prepares the digital information received to be sent to the sound synthesizer. The unit takes the digitized output of the flowmeter, which provides information about the start of inhalation (start of flow of gas from ventilator towards patient) and the start of exhalation (start of flow of gas from patient towards ventilator)., The unit also receives digitized information about $ETCO_2$ in mmHg at the end of each exhalation. The information is converted to a form that can be read by the sound synthesizer. Specifically, the onset and offset of inhalation and exhalation are represented as tones. The absolute value of volume flow is represented as the sound intensity (loudness) and/or sound quality (timbre or brightness), the values being read from a mapping function. The $ETCO_2$ value from the last breath is mapped to the pitch of the inhalation tone, the actual pitch value being read from a further mapping function. The pitch of the exhalation tone is set to a musical third interval below the inhalation tone.

The resulting information is sent to the sound synthesizer (see box E of FIG. 2). At the start of inhalation, the synthesizer plays a tone determined as described above. At the start of exhalation, the synthesizer plays a tone of the kind described above. The results are sent in real time to audio output (see box F of FIG. 2). As the absolute value of volume flow increases, sound intensity (loudness) and/or sound quality (timbre or brightness) increase, giving rise to a perception of rising and falling brightness of the sound within the inhalation and within the exhalation, and/or a rise and fall of loudness of the sound.

The user interface (see box G of FIG. 2) allows the user to adjust the overall volume of the respiratory sonification.

Figure 3:
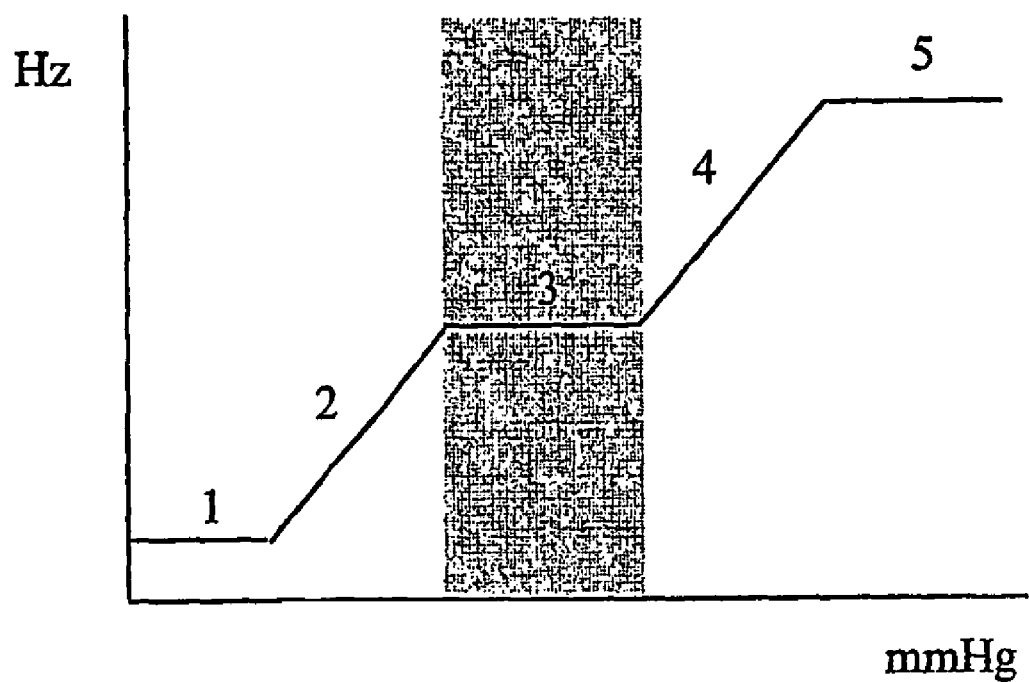
FIG. 3 shows the general form of mapping $ETCO_2$ in mmHg to pitch in Hz. Note the five regions: 1=lowest pitch used for lowest $ETCO_2$ levels, 2=pitch rising monotonically with $ETCO_2$, 3=pitch equivalent or near-equivalent pitch values across the normal range (shown in grey), 4=pitch rising monotonically with $ETCO_2$, and 5=highest pitch used for highest $ETCO_2$ levels.

The mapping of carbon dioxide concentration in mmHg to Hz is a non-linear function. The normal range for $ETCO_2$ is conventionally 38–42 mmHg. Across this range, mmHg is mapped to Hz in a way that produces very little change in Hz for a change in mmHg, producing a flat or nearly flat region in the mapping function. When mmHg moves lower than 38 or greater than 42, mmHg is mapping to Hz in a way that produces significant change in Hz for a change in mmHg, producing steep regions in the mapping function until extreme mmHg values are reached at which the function flattens and stays constant at extreme Hz values. The result is a piece-wise defined function whose: general form is illustrated in FIG. 3.

Figure 4:
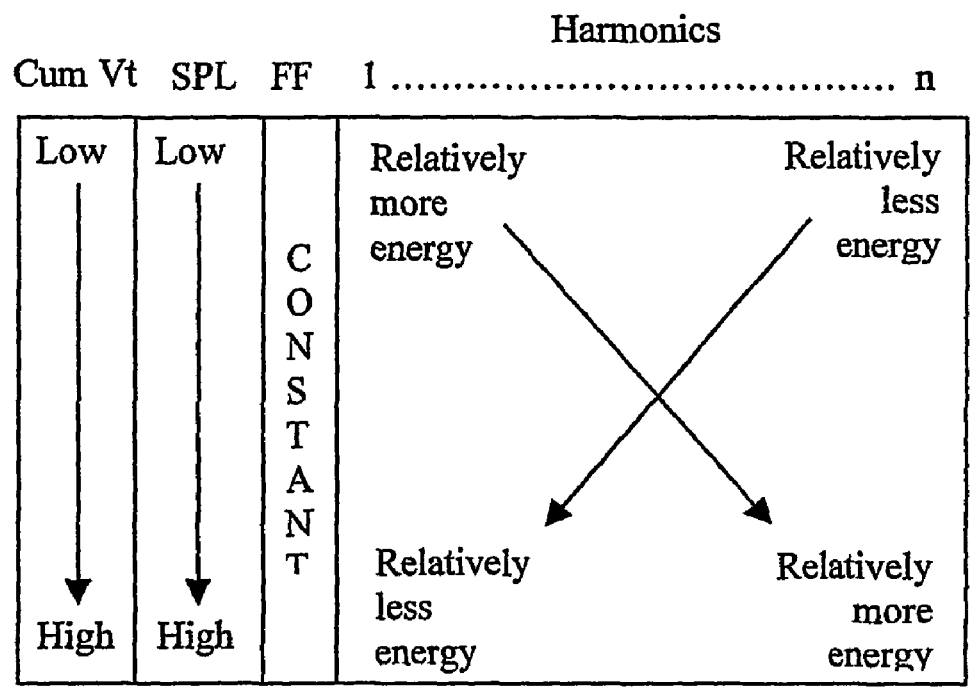
FIG. 4 shows the mapping of sound intensity (Sound Pressure Level or SPL) and/or sound quality (timbre or brightness) via harmonic structure to Cumulative Vt. As Cumulative Vt increases the fundamental frequency (FF) determined by $ETCO_2$ stays constant, but the distribution of sound energy over harmonics changes as shown.

The mapping of cumulative Vt to sound intensity (loudness) and/or sound quality (timbre or brightness) is performed according to the general schema shown in FIG. 4. As cumulative Vt increases, sound intensity increases and/or the relative intensity of sound in the lower harmonics vs higher harmonics changes. The auditory perception of low Cum Vt is of a rounded sound of audible volume, whereas the perception of high Cum Vt is of a much sharper, brighter sound and/or somewhat louder volume. As the value of Cum Vt changes within the inhalation or exhalation, the above changes to sound loudness and/or quality occur.

Empirical Evaluation of the Respiratory Sonification

We have completed some studies that examine the following issues:

H1 At least one sonification of respiratory parameters as described above will support judgements about respiratory status as effectively as pulse oximetry supports judgements about cardiovascular status.

H2 If respiratory sonification presents physiological information in a, way that is consistent with expert knowledge, then anaesthetists will perform better.

H3 Percentage correct responses for different physiological parameters will be sensitive to the changes in event rate.

H4 Percentage correct responses for different physiological parameters will be sensitive to the base rate probabilities of changes for different parameters.

H5 When participants perform a cognitively loading primary task, they will be able to monitor patient physiological status more effectively when patient data is sonified than when it is visually supported.

The invention will now be further described by way of reference only to the following non-limiting examples. It should be understood, however, that the examples following are illustrative only, and should not be taken in any way as a restriction on the generality of the invention described above.

EXAMPLE 1

Comparsion Various Methods of Respiratory Sonification

In comparing a preferred method of respiratory sonification with two older versions we made one hypothesis:

"At least one sonification of respiratory parameters will support judgements about respiratory status as effectively as pulse oximetry supports judgements about cardiovascular status."

All sonifications used a pure tone and mapped inhalation and exhalation to the upper and lower note of a musical third. Respiration rate was represented by a direct temporal mapping of inhalation and exhalation. For the "Varying" sonification, CumVt was represented by sound intensity (but our proposed respiratory sonification also maps sound quality (timbre or brightness) into CumVt). The integration of volume flow over time gave tidal volume. $ETCO_2$ was represented by a frequency modulation of the inhalation: exhalation minor third. Three variants were tested:

(1). The Varying sonification worked as described above, mapping $ETCO_2$ from the previous breath to the pitch of inhalation on the current breath, and using current breath volume flow to ramp sound intensity up to the peak which indicated the Vt for the present breath for inhalation or exhalation.

(2). The Even sonification was developed to test whether participants found it difficult to judge tidal volume by listening to the integration of volume flow of gas over time. The Even sonification used $ETCO_2$ and tidal volume (Vt) from the previous breath. $ETCO_2$ was mapped to the pitch of inhalation on the current breath and tidal volume was used to determine a constant, or even, sound intensity level for the inhalation and exhalation.

The Short sonification was developed to test whether participants found it difficult to extract information about respiration rate until the end of the breath. The Short sonification triggered the respiratory sonification at the start of each inhalation, as for the Varying and Even sonifications but it compressed the duration of the sonification into approximately one-third of its normal duration. At the same time, it preserved the relative duration of longer and shorter breaths and the ratio of inhalation to exhalation. The goal of developing the Short sonification was to see if performance was better when information about respiration rate could be extracted over a shorter period than the entire breath itself.

Our immediate focus was whether the mapping of physiological parameters to sound was intelligible. The study used a within-subjects design and participants were 23 tertiary-educated members of the general population with no medical or nursing training. Participants listened to an anaesthesia scenario produced from an anaesthesia simulation created from the Body™ library, SCHIL's Arbiter experimental environment providing the interface (Watson et al., 1999; 2000a; 2000b). When probed at semi-regular intervals, participants reported whether each parameter was abnormally high, normal, or abnormally low, and whether it was rising, steady, or falling. For volume, they were not asked about volume flow but about cumulative tidal volume, which is the integration of volume flow over time.

Figure 5A:
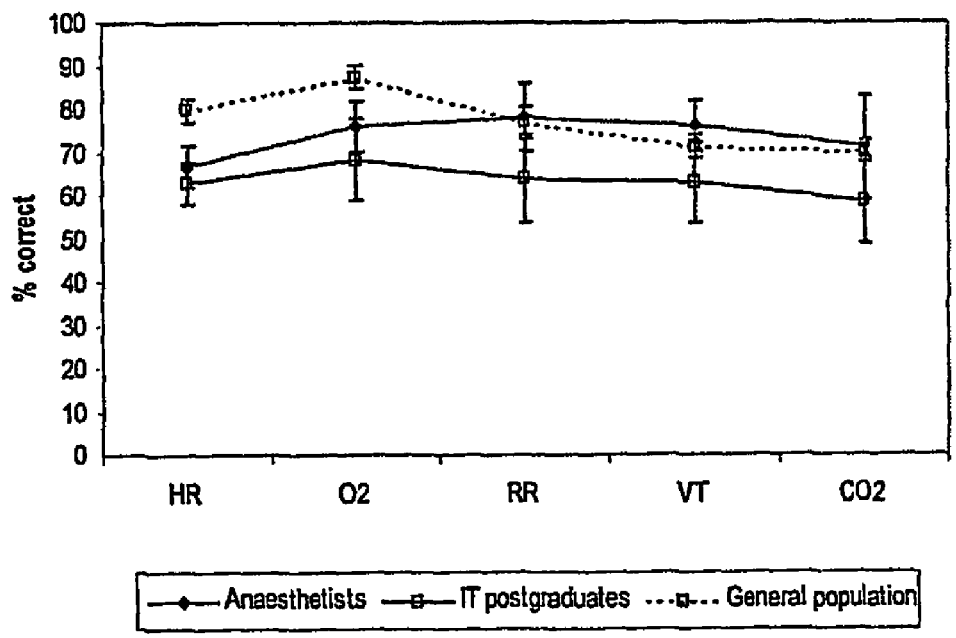
FIG. 5 shows the percentage correct responses to probes about whether parameters were (Upper graph) normal, abnormally high, or abnormally low or (Lower graph) holding steady, increasing, or decreasing for Examples 1 and 2.
Figure 5B:
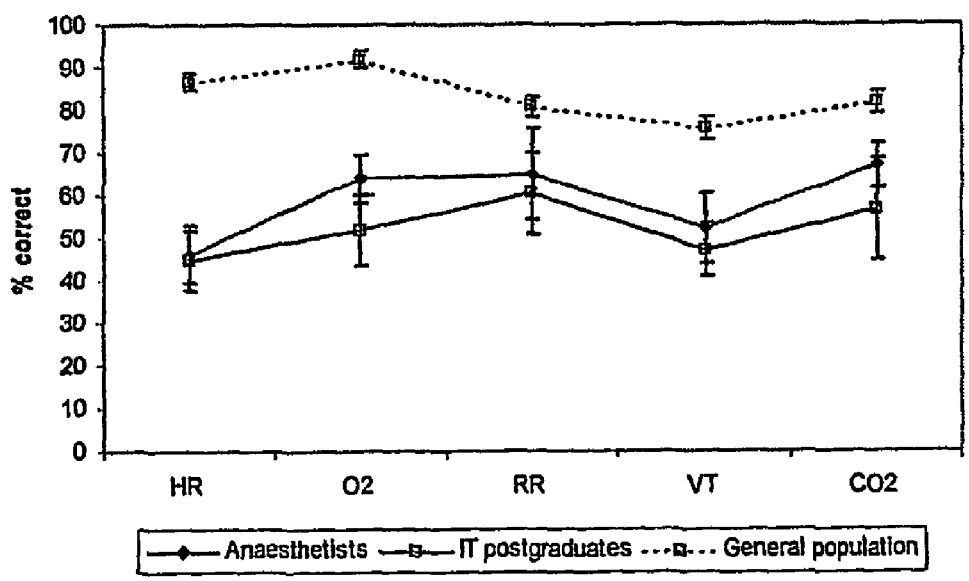

Results for the percentage of correct responses are shown in FIG. 5. There is an apparent superiority of pulse oximetry measures (HR and O2), but a deeper analysis of the results indicated to us that the a priori probability of signals strongly influenced the percentage of correct responses. Seldom-experienced changes had a higher proportion of "correct rejection" responses, artificially inflating the probably of correct responses overall. We performed signal detection studies to separate discriminability from response bias, but the test with probably the greatest ecological validity is the following.

In a conservative test of the intelligibility of sonified physiological parameters, we sought how many participants performed significantly better than chance given the number of answer alternatives, p(chance), and significantly better than would be expected if participants were responding randomly but with a response bias consistent with the base rate of non-normal or non-steady events, p(correct/baserate). In each case, the chance/baserate value had to lie in the lower 5% tail of a subject's distribution of responses for that item, in order for us to state that the participant had performed better than chance.

As the results in Table 1 show, the Varying sonification supported best performance across kinds of judgement, across tests, and across physiological parameters, although there were minor points where another of the three sonifications was superior.

TABLE 1

| | Better than | Sonification | HR | O₂ | RR | $V_T$ | CO₂ |
|---|---|---|---|---|---|---|---|
| Abnormality Judgment | p(chance) | Varying | 15 | 15 | 17 | 13 | 18 |
| | | Even | 10 | 13 | 13 | 5 | 8 |
| | | Short | 12 | 11 | 14 | 6 | 7 |
| | p(corr/br) | Varying | 15 | 15 | 17 | 13 | 18 |
| | | Even | 10 | 13 | 13 | 5 | 8 |
| | | Short | 12 | 11 | 14 | 6 | 7 |
| Directional Judgment | p(chance) | Varying | 16 | 21 | 16 | 18 | 19 |
| | | Even | 20 | 20 | 17 | 13 | 17 |
| | | Short | 20 | 22 | 14 | 17 | 16 |
| | p(corr/br) | Varying | 16 | 21 | 16 | 18 | 19 |
| | | Even | 20 | 20 | 17 | 13 | 17 |
| | | Short | 20 | 22 | 14 | 17 | 16 |

Number of participants for each sonification whose judgements were significantly better than chance. Underlined figures in white squares indicate that the number of participants is significantly different from chance at $p<0.05$; plain figures in white squares at $0.1>p>0.05$. Figures in grey cells indicate that results were not significantly different from chance.

The Varying sonification supported better judgements of abnormality that the other two sonifications, with RR and CO2 abnormalities apparently detected better than pulse oximetry measures HR and O2. Moreover, the varying sonification supported better across-the-board detection of directional changes, whereas the Even sonification was not quite as good for RR and the Short sonification was not quite as good for Vt. It is important to note that the Varying sonification led to markedly better performance.

EXAMPLE 2

Relative Performance of Anaesthrtists

We used the Varying sonification to test the relative performance of anaesthetists (medically trained) and post-graduate students in information technology who had no physiology training. The Example used anaesthesia scenarios that led to a more even distribution of abnormal events across the five parameters, and also to a greater absolute number of abnormal events or directional changes to report. Our hypotheses were:

H2 If the Varying sonification presents physiological information in a way that is consistent with expert knowledge, then anaesthetists will perform better than non anaesthetists.

H3 Percentage correct responses for physiological parameters will be sensitive to the different overall event rates in Example 1 and Example 2.

H4 Percentage correct responses for different physiological parameters will be sensitive to the base rate probabilities of changes for different parameters.

Results of a between-within subjects ANOVA indicated that H2 was supported: Anaesthetists performed better than IT postgraduates for judgements both of abnormality and of direction of change, $F(1,19)=20.604$, $p<0.001$ and $F(1,19)=10.341$; $p<0.01$, respectively.

H3 was also supported. To compare relatively similar participant groups, the results of the general population in Example 1 must be compared with those of the IT postgraduates in Example 2. The number of abnormal events per trial was 2.2 in Example 1 and 3.4 in Example 2 and the number of directional changes per trial was 2.5 in Example 1 and 4.1 in Example 2. Percentage correct responding was lower in Example 2 than Example 1: for abnormality judgements, $F(1,31)=23.8$, $p<0.0001$, and for directional judgements, $F(1,31)=61.59$, $p<0.0001$.

The lower accuracy of responding should not suggest that the sonifications are inherently unreliable. The event rate was sustained at a rate that would be seen only in the busiest parts of the most intense clinical situations. Clearly, pulse oximetry is effective in clinical settings, so the respiratory sonification should be compared with it in the current context.

H4 was also supported. In Example 2 events were more evenly distributed across pulse oximetry (HR and O2) and respiration (RR, Vt and $CO_2$) to reduce the previous bias towards respiration. FIG. 5 shows that the bias towards correct responding for HR and O2 is reduced. The respiratory sonification requires participants to distinguish three parameters whereas pulse oximetry requires them to distinguish only two parameters. Therefore the respiratory sonification is performing especially well if it produces performance in a comparable range to pulse oximetry.

Table 2 repeats the highly conservative analysis of intelligibility performed in Example 1, but for the 11 anaesthetists and 10 IT postgraduates tested in Example 2. Results suggest that anaesthetists perform better than IT postgraduates and that the respiratory sonification is doing as well if not better than pulse oximetry. Discrimination of directional changes was less effective for HR and Vt.

TABLE 2

| | Better than | | HR | $O_2$ | RR | $V_T$ | $CO_2$ |
|---|---|---|---|---|---|---|---|
| Abnormality Judgment | p(chance) | An | 11 | 10 | 11 | 11 | 11 |
| | | IT p/g | 10 | 4 | 9 | 7 | 8 |
| | p(corr/br) | An | 7 | 8 | 11 | 11 | 10 |
| | | IT p/g | 5 | 3 | 7 | 7 | 7 |
| Directional Judgment | p(chance) | An | 5 | 11 | 11 | 7 | 11 |
| | | IT p/g | 4 | 6 | 9 | 3 | 7 |
| | p(corr/br) | An | 1 | 9 | 6 | 7 | 9 |
| | | IT p/g | 3 | 3 | 5 | 3 | 5 |

Number of participants from each group whose judgements were significantly better than chance. Underlined figures in white squares indicate that the number of participants is significantly different from chance at $p<0.05$; plain figures in white squares at $0.1>p>0.05$. Figures in grey cells indicated that results were not significantly different from chance. Total number of anaesthetists is 11 and of IT postgraduates is 10.

Overall, the results of Example 2 obtained with no prior experience by anaesthetists or IT postgraduates to respiratory sonification and only 15 minutes of initial familiarisation, are highly encouraging of the viability of respiratory sonification for clinical settings.

EXAMPLE 3

Monitoring Patient Status

In this example we examined participant's ability to use the respiratory sonification when performing other tasks. Monitoring was supported by sonification only, sonification plus a visual display, and a visual display only. The hypothesis was as follows:

H5 When participants perform a cognitively-loading primary task, they will be able to monitor patient physiological status more effectively when patient data is sonified than when it is visually supported.

Figure 6:
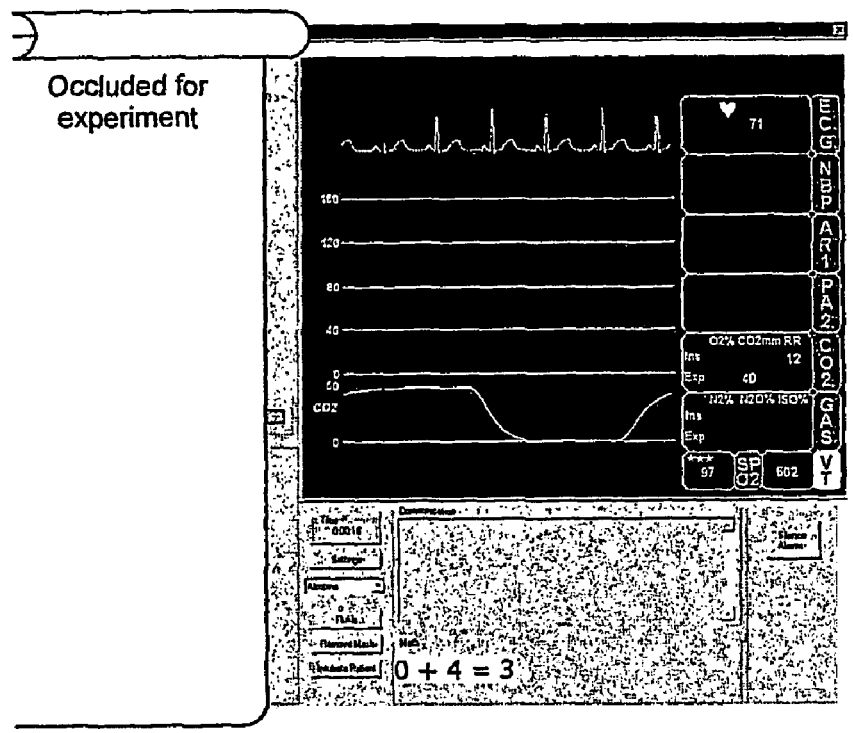
FIG. 6 shows the anaesthesia simulation as used in Example 3. Controls for anaesthesia gases and ventilator are occluded.

To test this hypothesis we constructed a very conservative test. Participants performed a primary task in which they were required to make true/false judgements about simple arithmetic expressions (see FIG. 6) with a new expression occurring every 10 seconds. This had some similar characteristics to drug dosage calculations that a clinician might need to perform while monitoring patient status. At the same time, they performed the secondary physiological monitoring task, as in previous Examples. The physiological monitoring task was presented in one of three formats, varied within-subjects:

Sonification alone (S condition). No patient information appeared or could be called up on the computer screen.

Visualization alone (V condition). Physiological readouts were not continually present. Participants had to touch ("query") the relevant part of the screen to see the current value for five seconds ("withholding" procedure).

Sonification plus Visualization (SV condition). Again, the Visualization condition used the withholding procedure.

The 10-second arrival rate of arithmetic problems gave participants in the V and SV conditions enough time to query all parameters before the next arithmetic expression appeared. Although sonification is intended to provide information where visual information is unavailable or inconvenient, in this first test we set up the best possible conditions for the visual display to succeed. If S nonetheless leads to superior performance, then such superiority would have been observed under conditions in which it is possible to do the task visually to the same level of performance. If S leads to the same level of performance as for V, however, then we know that sonification does not support worse performance than a visual display does. The results will therefore provide a conservative baseline comparison between the three conditions. It is assumed thereafter that as the time between arithmetic problems decreases, the S and probably also the SV conditions would show increasingly effective monitoring performance.

Participants experienced plausible operating room scenarios. Approximately every minute, participants were asked to make judgements about any recent abnormality and any direction of change within the last minute on one of the five parameters. Questions were evenly distributed across parameters, so there was no in-built bias in questioning towards any parameter.

Primary (arithmetic) task performance was analysed using a between-within subjects ANOVA. Results are shown in FIGS. 7a and b on the x axis of each graph. There was a significant effect of Group, $F(1,19)=9.54$, $p<0.01$, with Anaesthetists performing better than IT postgraduates. Modality was significant, $F(2,38)=10.05$, $p<0.001$, with responses most accurate in the S condition, followed by V and SV. A Newman-Keuls analysis showed that responding in the S condition was significantly more accurate than in either the V or the SV conditions.

Figure 8A:
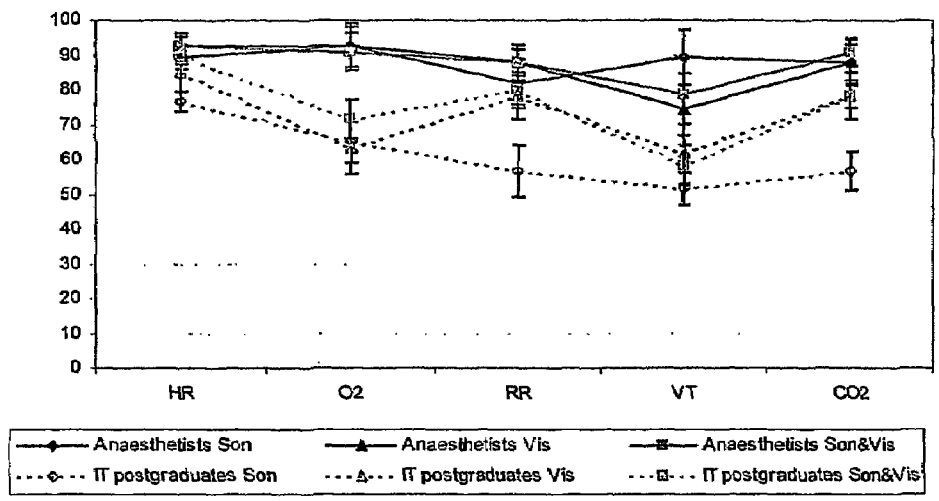
FIGS. 8a and 8b show the anaesthetists' and IT postgraduates' judgements compared across monitoring modalities (S, V and SV) and physiological parameters.

Results for secondary task abnormality judgements are shown on the y axis of FIG. 7a. Group was highly significant, $F(1,19)=44.69$, $p<0.0001$, with Anaesthetists much better than IT postgraduates at reporting abnormalities. Modality was significant, $F(2, 38)=5.69$, $p<0.01$, with performance worst with the S condition, but only because of IT postgraduates' poor performance. In fact, Modality interacted strongly with Group, $F(2,38)=6.49$, $p<0.01$. As FIGS. 7a and 7b show, Anaesthetists judged abnormalities equally well across all three modalities whereas IT postgraduates did particularly poorly with S alone. Parameter was also significant, $F(4,76)=13.83$, $p<0.0001$, with Vt showing worst performance and HR showing best performance (see FIG. 8a). However the poorer performance with Vt was much reduced for Anesthetists compared with the IT postgraduates, contributing to a Group by Parameter interaction, $F(4,76)=4.08$, $p<0.01$.

Figure 8B:
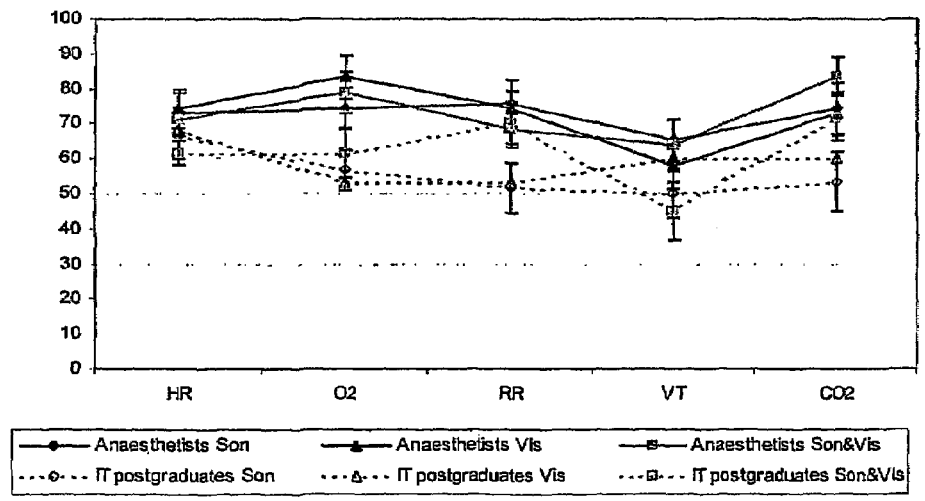

Results for secondary task judgements of direction of change are shown on the y axis of FIG. 7b. Group was significant, $F(1,19)=41.06$, $p<0.0001$, with Anaesthetists much better than IT postgraduates. There were no main effects or interactions with Modality, but Parameter was significant, $F(3,76)=6.06$, $p<0.001$, with Vt showing worst performance (see FIG. 8b).

There was also a significant drop in the frequency of querying in condition SV compared with V, but only for Anaesthetists, and then only for HR and O2, the most familiar pulse oximetry sonifications. With further experience, and with performance feedback, participants would probably develop greater self-confidence in their ability to extract information from sonification and reduce visual monitoring for respiratory parameters as well. Whether this is the case is currently under investigation.

Overall, Example 3 showed that sonification allowed anaesthetists to maintain monitoring accuracy while performing significantly better on an arithmetic task than when visual support was available. IT postgraduates showed a tradeoff between the monitoring task and the arithmetic task. Sonification led to worse monitoring performance, probably because of IT postgraduates' lack of physiological training, but to better performance on the arithmetic task, probably because no further attention to the monitoring task would improve performance.

Vt appears to be slightly less effective than other sonified dimensions in Examples 1 and 2, where sonification with no redundant visual information is examined. However that fact that in Example 3 judgements about Vt have equivalent levels of accuracy across V, SV, and S conditions suggests that the less accurate performance with Vt is endemic to Vt itself rather than to any modality. Given the scenarios used, Vt shows many small fluctuations making it more challenging to monitor rather than a few large fluctuations, which would affect all modality conditions. In fact, anaesthetists abnormality judgements for Vt appear to be somewhat better supported with sonification alone (S condition) than others.

CONCLUSIONS

Taken together, the results of Examples 1 to 3 show that with a minimal level of familiarization, participants can monitor respiratory status with the Varying respiratory sonification as well as they can monitor cardiovascular status with the pulse oximetry sonification. Example 3 shows that when anaesthetists carry out a distracting task at the same time as monitoring, as is often the case in the operating room, sonification helps them time-share. However, instead of boosting monitoring performance while a distracting task is done, sonification allowed anaesthetists' monitoring performance to be sustained at high levels while performance at the distracting task become better. In ongoing research we are graduating the level of difficulty of the primary task and expect to see greater differences emerge across conditions for patient monitoring, increasingly favouring sonification. We are also adding brightness to the sonification for Vt to determine its effects.

Results of our studies also suggest that researchers must be cautious about making claims about the superiority or otherwise of specific display conditions until the influence of a priori event probability and the size of changes has been taken into account. The relative accuracy of judgements for the five physiological parameters various across Examples 1, 2 and 3 because of these factors.

In summary, sonification of patient physiology beyond traditional pulse oximetry appears a viable and useful adjunct when monitoring patient state. Sonification may help anaesthetists maintain high levels of awareness of patient state and at the same time do other tasks more effectively than when relying upon visual monitoring of patient state. The Varying respiration sonification appears to be effective in this role and it presents some advantages over related respiratory sonifications.

REFERENCES

Fitch, W. T., & Kramer, G. (1994). Sonifying the body electric: Superiority of an auditory over a visual display in a complex, multivariate system. In G. Kramer (Ed.), *Auditory display: Sonification, audification, and auditory interfaces.* Reading, Mass.: Addison-Wesley.

Kramer, G. (1994), *Auditory display: Sonification, audification, and auditory interfaces.* Reading, Mass.: Addison-Wesley.

Loeb, R. G., & Fitch, W. T. (2000). *Laboratory Evaluation of an Auditory Display Designed to Enhance Intra-Operative Monitoring.* The Society for Technology in Anesthesia Annual Meeting 13–15 Jan. 2000 Orlando. Abstract from anestech.org/publications. File: Annual-2000/Loeb.html Tinker, J., Dull, D., Caplan, R., Ward, J., & Cheney, F (1989). Role of monitoring devices in prevention of anesthetic mishaps: a closed claims anlaysis. *Anesthesiology,* 71, 541–546.

Webb, R., van der Walt, J., Runciman, W., Williamson, J., Cockings, J., Russell, W. J., & Helps, S. (1993). Which monitor? An analysis of 2000 incident reports. *Anaesthesia and Intensive Care,* 21, 529–542.

Seagull, F. J., & Sanderson, P. M. (2001a). Anesthesia alarms in surgical context: An observational study. *Human Factors,* 43(1), 66–77.

Watson, M., & Sanderson, P. M. (1998). Work domain analysis for the evaluation of human interaction with anaesthesia alarm systems. *Proceedings of the Australian/New Zealand conference on Computer-Human Interaction* (OzCHI98). Los Alamitos: IEEE Computer Society. Pp 228–235.

Watson, M., Russell, W. J., & Sanderson, P. (1999). Ecological interface design for anesthesia monitoring. *Proceedings of the Australian/New Zealand conference on Computer-Human Interaction* (OzCHI99). Wagga Wagga: Charles Sturt University. Pp 78–84.

Watson, M., Russell, W. J., & Sanderson, P. (2000a). Anesthesia monitoring, alarm proliferation, and ecological interface design. *Australian Journal of Information Systems,* 7(2), 109–114.

Watson, M., Sanderson, P., & Russell, J. W. (2000b). Alarm noise and end-user tailoring: The case for continuous auditory displays. *Proceedings of the Fifth Annual Symposium on Human Interaction with Complex Systems* (HICS2000). Urbana, Ill.: Beckman Institute. Pp.75–80.

The invention claimed is:

1. A respiratory sonification monitoring system for monitoring respiration and/or, gas exchange in a subject including in combination;
   capnometric means for measuring respiratory carbon dioxide concentrations,
   flowmeter means for measuring gas flow and volume of said gas flow by the integration of the gas flow with respect to time,
   signal processing means adapted to process into digital information, signal output from the capnometric means and the flowmeter means throughout the subject's breathing process,
   sound synthesizer means adapted to convert said digital information into a synthesized audio output which is not a simulated realistic body sound,
   wherein in use, changes in respiratory flow during inhalation and exhalation, and changes in end tidal carbon dioxide concentrations ($ETCO_2$) and cumulative tidal volume (cumVt) of the subject are represented as changes in the synthesized audio.

2. A respiratory sonification monitoring system for monitoring respiration and/or gas exchange in a subject as claimed in claim 1, wherein the capnometric means is an electronic carbon dioxide monitor with signal output means whereby end tidal carbon dioxide concentrations ($ETCO_2$) can be measured and recorded.

3. A respiratory sonification monitoring system for monitoring respiration and/or gas exchange in a subject as claimed in claim 1, wherein the flow meter means is an electronic respiratory flow meter wherein cumulative volume measurements can be calculated by the electronic integration of the flow signal over a given time interval.

4. A respiratory sonification monitoring system for monitoring respiration and/or gas exchange in a subject as claimed in claim 1, wherein the signal processing means is an analogue to digital signal converter wherein analogue signals from the capnometric means and the flow meter means are converted into digital information.

5. A respiratory sonification monitoring system for monitoring respiration and/or gas exchange in a subject as claimed in claim 1, wherein the sound synthesizer means has audio pre-amplifier means which conditions the digital information and converts it to a synthesized audible tone which can be heard through a loudspeaker, headphone or ear piece.

6. A respiratory sonification monitoring system for monitoring respiration and/or gas exchange in a subject as claimed in claim 1, wherein inhalation is represented as an upper note of a musical third interval and exhalation is represented as the lower note that comprise a pair of tones.

7. A respiratory sonification monitoring system for monitoring respiration and/or gas exchange in a subject as claimed in claim 6, wherein end tidal carbon dioxide concentration ($ETCO_2$) is represented by a change in relative pitch across respiratory cycles wherein the pitch of the exhalation tone is set at a minor third interval below that of the inhalation tone, and wherein a high $ETCO_2$ would be represented by a pair of tones at a high pitch and low $ETCO_2$ would be represented by the pair of tones at a low pitch.

8. A respiratory sonification monitoring system for monitoring respiration and/or gas exchange in a subject as claimed in claim 1, wherein there are five regions of pitch changes wherein the lowest, pitch level reflects end tidal-carbon dioxide concentrations below an arbitrarily low $ETCO_2$ concentration value and the highest pitch reflects end tidal carbon dioxide concentrations values above an arbitrarily high $ETCO_2$ concentration value.

9. A respiratory sonification monitoring system for monitoring respiration and/or gas exchange in a subject as claimed in claim 1 wherein the measured end tidal carbon dioxide levels can be graphically represented as a frequency modulation of the minor third interval note pairs of inhalation and exhalation tones.

10. A respiratory sonification monitoring system for monitoring respiration and/or gas exchange in a subject as claimed in claim 1, wherein cumulative tidal volume (cumVt) is calculated by integrating volume flow (Vt) over time and can be represented by sound intensity (loudness) and/or sound quality (timbre or brightness) and wherein the cumulative tidal volume (cumVt) can be represented by the amplitude of more than one spectral component of the sound, resulting in perceptible differences in timbre or harmonic brightness of the audible tones.

11. A respiratory sonification monitoring system for monitoring respiration and/or gas exchange in a subject as claimed in claim 1, wherein there is user interface means typically a volume control to control and adjust the overall volume of the sonification.

12. A respiratory sonification monitoring system for monitoring respiration and/or gas exchange in a subject as claimed in claim 11 wherein the user interface means is an electronic or electromechanical volume control means.

13. A respiratory sonification monitoring system for monitoring respiration and/or gas exchange in a subject as claimed in claim 1, wherein the respiratory monitoring apparatus is not necessarily used in isolation but alongside prior art pulse oximetry systems.

14. A method of monitoring human respiration and gas exchange in a subject during anaesthesia or intensive care including the steps of connecting a flaw meter to an anaesthesia circuit to measure the rate at which gas is flowing into (inhalation) and out of (exhalation) a patient's lungs, connecting a capnometer to the anaesthesia circuit to measure carbon dioxide concentrations, inclusive of end tidal carbon dioxide concentrations ($ETCO_2$) at the end of each exhalation, processing signals from the flow meter and the capnometer by signal processing means into digital information, converting the digital information by sound synthesizer means into audio output, wherein, the onset and offset of inhalation and exhalation are represented as changes in tone of a synthesized musical note, the value of cumulative tidal volume (cumVt) is represented as sound intensity (loudness) and/or sound quality (timbre or brightness) of the tone, and end tidal carbon dioxide levels ($ETCO_2$) are represented by relative changes in pitch across respiratory cycles, wherein the pitch of the exhalation tone is set at a minor third interval below that of the inhalation tone.

* * * * *

UNITED STATES PATENT AND TRADEMARK OFFICE
CERTIFICATE OF CORRECTION

PATENT NO. : 7,070,570 B2 Page 1 of 1
APPLICATION NO. : 10/488150
DATED : July 4, 2006
INVENTOR(S) : Sanderson et al.

It is certified that error appears in the above-identified patent and that said Letters Patent is hereby corrected as shown below:

Column 16, Line 41, ~~Claim 14~~:

Delete "flaw" and insert therefor -- flow --.

Signed and Sealed this

Twelfth Day of September, 2006

JON W. DUDAS
*Director of the United States Patent and Trademark Office*